United States Patent [19]

Jungck

[11] 4,105,509
[45] Aug. 8, 1978

[54] COMBINATION MEASURING AND REFERENCE POTENTIAL ELECTRODE AND METHOD OF MEASURING PH IN SAMPLES SUBJECT TO LARGE VOLTAGE GRADIENTS

[75] Inventor: Philip R. Jungck, Horsham, Pa.

[73] Assignee: Leeds & Northrup Company, North Wales, Pa.

[21] Appl. No.: 831,216

[22] Filed: Sep. 7, 1977

Related U.S. Application Data

[63] Continuation of Ser. No. 554,287, Feb. 28, 1975, abandoned.

[51] Int. Cl.² .................................. G01N 27/30
[52] U.S. Cl. .................... 204/1 T; 204/195 R; 204/195 F; 204/195 G
[58] Field of Search .............. 204/195 F, 195 G, 1 H, 204/1 T, 195 R; 128/2 E, 2.1 E; 536/114

[56] References Cited

U.S. PATENT DOCUMENTS

| | | | |
|---|---|---|---|
| 3,236,831 | 2/1966 | Schweiger | 536/114 |
| 3,264,205 | 8/1966 | Leonard et al. | 204/195 F |
| 3,498,899 | 3/1970 | Kater et al. | 204/195 F |
| 3,594,263 | 7/1971 | Dwyer et al. | 161/160 |
| 3,741,884 | 6/1973 | Deushane et al. | 204/195 F |
| 3,957,612 | 5/1976 | Niedrach et al. | 204/195 M |
| 3,973,555 | 8/1976 | Moller et al. | 128/2 E |

OTHER PUBLICATIONS

Galaxy XB Xanthan Gum, pp. 3-7, General Mills Chemicals, Inc.

*Primary Examiner*—G. L. Kaplan
*Attorney, Agent, or Firm*—W. G. Miller; R. F. MacKay

[57] ABSTRACT

A combination measuring and reference electrode which has a large annular reference junction around the centrally located measuring electrode filled with a gel electrolyte so as to provide an equal resistivity at the junction in all radial sectors to prevent a net voltage difference between the measuring and reference electrodes due to voltage gradients in the sample.

12 Claims, 1 Drawing Figure

U.S. Patent
Aug. 8, 1978
4,105,509
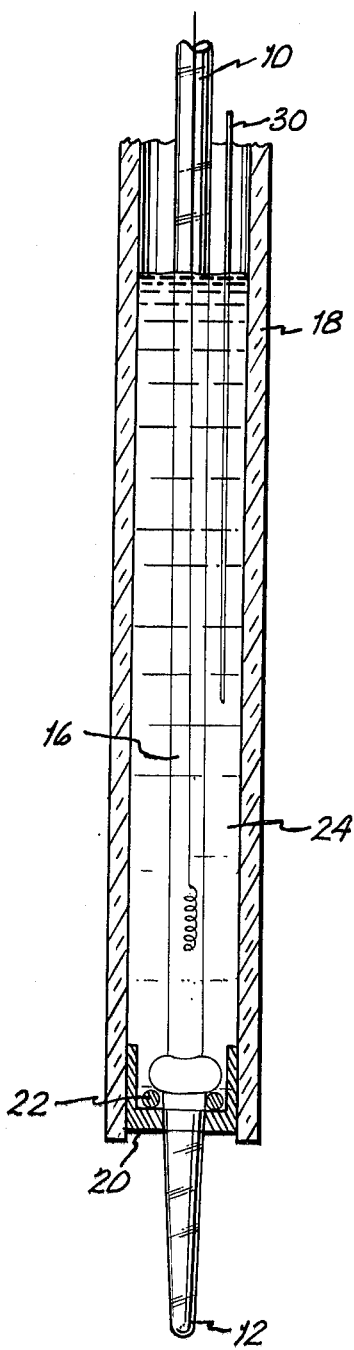

COMBINATION MEASURING AND REFERENCE POTENTIAL ELECTRODE AND METHOD OF MEASURING PH IN SAMPLES SUBJECT TO LARGE VOLTAGE GRADIENTS

This application is a continuation of Ser. No. 554,287, filed Feb. 28, 1975, now abandoned.

BACKGROUND OF THE INVENTION

This invention relates to combination electrodes of the type which include both the measuring and reference electrodes of a potentiometric electrode system. The electrode combination may be a pH electrode, other specific ion electrodes or a redox electrode.

More particularly the invention relates to a structure for a combination electrode which minimizes the effects of harsh environments such as voltage gradients within a process sample.

In the past there has been considerable difficulty in getting a consistent pH measurement, for example, in plating baths and chlorine production cells because of the large voltage gradients which exists in such process samples. For example, in a chlorine production cell the bath may carry 80,000 amperes of d.c. current and it may be at 250 volt d.c. above ground. In such applications pH electrodes of all available types have been considered and many complicated arrangements have been attempted to avoid the effects on the pH measurement of the high voltage gradients occurring in the bath. Until the invention of the present combination electrode previous attempts to obtain consistent, dependable pH measurements in such baths have not been successful.

As is well known in electrochemical measurements, and specifically the potentiometric type measurements, there is usually utilized a measuring half cell and a reference half cell. The measuring half cell may be a high impedance device such as a glass electrode, for the determination of pH, that generates a potential with respect to the liquid sample medium such that that potential is a function of the hydrogen ion concentration of the sample. The reference electrode provides a potential that is substantially independent of the variable composition of the sample. The reference half cell comprises generally a piece of metal in contact with a mass of sparingly soluble salts of that metal, the assembly being placed in a salt bridge solution. The salt bridge solution has a nonmetallic ion in common with the sparingly soluble metal salt. In order to establish contact between the metal and the sample solution there is generally provided a reference junction that allows a constant diffusion of the salt bridge solution from the reference electrode when the electrode is wetted by the sample. Well known examples of reference half cells, commonly referred to as reference electrodes, are the silver-silver chloride electrodes and the calomel electrode. The electrolyte or salt bridge solution for both types is usually potassium chloride.

Many different structures have been utilized to provide the reference junction of the reference electrode. Such reference junction structures have included the use of thin ceramic coatings on the inner portion of the body of the reference electrode which provides a very limited leakage path between the reference electrode electrolyte and the sample. Such arrangements have been suggested where the centrally oriented glass electrode for pH measurement is surrounded by the body portion of the reference electrode whose end is lined with a ceramic coating with the space between that ceramic coating and body reference electrode being sealed by an elastomeric element.

Others have utilized elastomeric elements sealing the cavity between a central pH electrode and a surrounding electrode body where the body of the glass electrode has been roughened to provide for a small amount of leakage of the reference electrode electrolytes. In both of the above mentioned arrangements the leakage of the electrolyte takes place over a complete 360° arcuate span and all of these prior devices have utilized liquid electrolytes which require, under normal conditions, frequent replenishment. These prior art devices all have the disadvantage of providing a reference junction whose resistivity is not uniform throughout the 360° span over which it is effective and hence electrodes using such arrangements are subject to erroneous measurements when the electrodes are used in samples subject to high voltage gradients.

The arrangements of the prior art described above also generally have the disadvantage of being subject to clogging, particularly where the sample is likely to coat or foul the leaking region.

It is an object of the present invention to provide a combination measuring reference electrode which would be substantially free from the disadvantages of the prior art when utilized in samples subject to voltage gradients.

SUMMARY OF THE INVENTION

The combination electrode of the present invention provides a measuring electrode with a reference electrode having a body portion surrounding the body portion of the measuring electrode. The reference electrode utilizes an annular element of porous material positioned to close the cavity between the body portions of the measuring and reference electrodes and provide a large annular area exposed to the sample in close proximity to the measuring electrode and concentric therewith so that in conjunction with the electrolyte of the reference electrode there is formed a reference junction having a uniform resistance over all radial segments. The electrolyte of the reference electrode is contained in the cavity between the body portions of the reference and measuring electrode and is a saturated gel.

BRIEF DESCRIPTION OF THE DRAWING

The DRAWING shows a sectional view of part of a combination measuring and reference electrode of the type used for measuring pH.

DESCRIPTION OF THE PREFERRED EMBODIMENT

Referring to FIG. 1, there is shown the lower portion of a combination pH electrode which includes a centrally located glass electrode having a cylindrical body portion 10 closed at its lower end by a pH sensing glass membrane 12. The glass electrode contains an internal pH buffer solution including potassium chloride. There is immersed in that buffer solution a chloridized silver wire 16.

The centrally oriented glass electrode is surrounded by the cylindrical body portion of the reference electrode, namely, body portion 18. An annular element 20 of porous material is provided to close off the cavity between the body portion of the measuring and reference electrodes. The element 20 is sealed to the glass electrode by means of the 0 ring 22 so as to form a liquid-tight seal therebetween. The element 20 as shown in the drawing consists of a thick porous cylinder which may desirably have a density that is uniform so that the reference junction for the electrode combination it provides has approximately the same specific resistance for any equal segment of the porous element when the reference electrode is filled with electrolyte. The porous material at which the reference junction is formed may, for example, be cordierite. It is desirable that the electrolytic resistance of the reference junction should be low, that is in the order of 1,000 ohms, and have relatively large area in the order of 50 square millimeters.

The electrolyte contained in the cavity 24 between the body portion of the reference and measuring electrodes preferably consists of a gel such as xantham, which is a complex polysaccharide having the characteristic that it has nearly constant viscosity over the temperature range of zero to 130° Centigrade. Other materials such as methylcellulose, which thickens at higher temperatures, can be used as the gel where desirable. Included in the gel are sufficient quantities of potassium chloride crystals and silver chloride crystals to maintain complete saturation over an operating temperature, for example, of a range of −5 to +110° Centigrade. Thus, the electrolyte of the reference electrode is a non-flowing electrolyte which depends on diffusion through a relatively open and large area reference junction of the type provided by the element 20.

The electrolyte of the reference junction is contacted by a silver wire 30 which forms the silver-silver chloride element for the reference electrode.

When utilizing the electrode structure of the figure in a process having currents passing through them which cause voltage differentials between any two points not at 90° to the current flow it has been found that consistant and dependable measurements can be obtained. The same results can be obtained when using the electrode in samples having a low specific conductance wherein there can be generated potentials due to electron shearing. Thus, the electrode structure of the figure is useful in plating baths, chlorine production cells, and in measurements in flowing low conductivity water where streaming current potentials can exist.

The combination electrode of the figure with its centrally located measuring electrode and continuous annular element forming the reference junction for the reference electrode obtains a measurement unaffected by the voltage gradients regardless of the positioning of the combination electrode. This results because the orientation of the measuring electrode and the reference junction of the reference electrode results in voltages due to the voltage gradient in the sample which occurs between the measuring electrode and the reference junction are always equal and opposite. Thus, the final result is that the net effective external voltage due to the voltage gradient in the sample is zero regardless of the direction of orientation of the voltage field with regard to the electrode. Consequently, any changes in the process that change the direction of the voltage field, such as placing material to be plated within a plating bath, will not affect readings obtained with the electrode of this invention. The conventional structures of the measuring and reference electrodes, whether they be separate probes or of a single-probe variety such as the prior art arrangements for combination electrodes, effectively bridge across a potential in the field in the sample so as to add to the potential detected by the electrode system, and hence that measured by any associated measuring instrument. The potential measured with prior art systems will be the voltage between the measuring and reference electrodes due to the pH of the sample plus the potential due to the voltage gradient in the sample.

Using the gel electrolyte saturated with potassium chloride and containing an excess of potassium chloride crystals, the reference electrode functions by the diffusion of potassium chloride from the reference electrode reservoir in the cavity between the measuring and reference electrode bodies when the porous reference is wetted by the sample. The gel, of course, controls the rate of diffusion and serves to provide a combination electrode wherein the electrolyte of the reference electrode does not require large storage volume and maintains a useful electrode system for a long period of time without replenishment of the electrolyte. By virtue of the lack of need for an external reservoir for the reference electrode electrolyte there results a reduction in the danger from electrical shock when the electrode system is used in samples that are operated off ground potential.

What is claimed is:

1. A combination potentiometric electrode for measuring in samples having high voltage gradients, comprising,
   a measuring electrode having a body portion closed at one end with a sensing member; and
   a reference electrode having,
      a body portion positioned to surround the body portion of said measuring electrode,
      a saturated gel electrolyte in the cavity formed between the measuring and reference electrodes, and
      an annular element of substantially uniform porous material positioned between the body portions of said measuring and reference electrodes to close said cavity and provide a large area exposed for diffusion of said electrolyte into said sample to thereby form a reference junction so that said reference junction is in close proximity to the sensing member and concentric therewith to present a uniform resistance over all segments of the reference junction.

2. A method for measuring with a pH measuring instrument the pH of a sample having large voltage gradients which comprises the steps of:
   immersing in said sample a combination pH electrode having;
      a measuring electrode with a body portion closed off at one end with a pH sensing glass, and
      a reference electrode whose body portion surrounds the body portion of the measuring electrode forming a cavity therebetween filled with a gel electrolyte which is retained therein by an annular porous element providing a relatively large area of contact between said element and said sample so that the electrolyte can diffuse into the sample forming a reference junction concentric with the pH sensing glass of the measuring electrode to provide a uniform low resistance over all segments of the reference junction; and
   detecting the pH of the sample by connecting said instrument across the combination electrode.

3. A combination potentiometric electrode comprising;
   a measuring electrode having a body portion closed at one end with a sensing member; and
   a reference electrode having,
   a body portion positioned to surround the body portion of said measuring electrode,
   a saturated gel electrolyte in the cavity formed between the measuring and reference electrodes, and
   an annular element of substantially uniform porous material positioned between the body portions of said measuring and reference electrodes to close said cavity and provide a large area exposed for diffusion of said electrolyte into a sample to thereby form a reference junction.

4. A combination potentiometric electrode as set forth in claim 3 in which said gel electrolyte is xanthan.

5. A pH electrode combination comprising;
   a measuring electrode having
   a body portion,
   a pH sensing glass membrane closing one end of said body portion,
   a pH buffer solution containing potassium chloride retained in said body portion in contact with the internal surface of said membrane, and
   a chlorized silver wire maintained in contact with said buffer solution to provide an electrical measuring-electrode connection; and
   a reference electrode having
   a body portion supported concentric to the body portion of said measuring electrode,
   a hollow cylinder of porous material adapted to be fitted around said body portion of said measuring electrode and within the body portion of said reference electrode so as to provide a fluid-tight closure therebetween with a large area exposed for contact with samples to be measured,
   a gel electrolyte in the cavity between said measuring and reference electrode bodies and in contact with said cylinder to provide a reference junction for said electrode, said gel including sufficient quantities of potassium chloride crystals and silver chloride crystals to maintain saturation over the operating temperature of the electrode combination, and
   a silver wire in contact with said gel electrolyte to provide an electrical reference-electrode connection.

6. A pH electrode as set forth in claim 5 in which the gel electrolyte is of xanthan.

7. A combination potentiometric electrode, comprising;
   a measuring electrode having a body portion closed at one end with a sensing member; and
   a reference electrode having,
   a body portion positioned to surround the body portion of said electrode,
   a gel electrolyte in the cavity between said measuring and reference electrode bodies, said gel including sufficient quantities of potassium chloride crystals and silver chloride crystals to maintain saturation over the operating temperature of the electrode combination, and
   an annular element of substantially uniform porous material positioned between the body portions of said measuring and reference electrodes to close said cavity and provide a large area exposed for diffusion of said electrolyte into the sample being measured to thereby form a reference junction.

8. An electrode as set forth in claim 7 in which the sensing member is a glass member for sensing pH.

9. A pH electrode combination as set forth in claim 7 in which said annular element is sealed to the body of the measuring electrode by an O ring.

10. A combination potentiometric electrode as set forth in claim 7 in which the gel electrolyte is of xanthan.

11. A potentiometric electrode system, comprising;
    a measuring electrode; and
    a reference electrode having,
    a body portion,
    a gel containing crystals of a salt forming an electrolyte in amount sufficient to maintain saturation over the operating temperatures of the electrode system, and
    a uniform porous material for containing said electrolyte in said reference electrode while providing a large area exposed to the samples being measured for diffusion of said electrolyte in said sample.

12. A potentiometric electrode system as set forth in claim 11 in which the gel electrolyte is of xanthan.

* * * * *